(12) United States Patent
Knebel et al.

(10) Patent No.: US 10,429,301 B2
(45) Date of Patent: Oct. 1, 2019

(54) METHOD AND APPARATUS FOR INVESTIGATING A SAMPLE BY MEANS OF OPTICAL PROJECTION TOMOGRAPHY

(71) Applicant: LEICA MICROSYSTEMS CMS GMBH, Wetzlar (DE)

(72) Inventors: Werner Knebel, Kronau (DE); Wernher Fouquet, Mannheim (DE); Frank Sieckmann, Eppingen (DE)

(73) Assignee: Leica Microsystems CMS GmbH, Wetzlar (DE)

(*) Notice: Subject to any disclaimer, the term of this patent is extended or adjusted under 35 U.S.C. 154(b) by 0 days.

(21) Appl. No.: 15/104,997

(22) PCT Filed: Dec. 17, 2014

(86) PCT No.: PCT/EP2014/078335
§ 371 (c)(1),
(2) Date: Jun. 16, 2016

(87) PCT Pub. No.: WO2015/091713
PCT Pub. Date: Jun. 25, 2015

(65) Prior Publication Data
US 2016/0320301 A1 Nov. 3, 2016

(30) Foreign Application Priority Data
Dec. 17, 2013 (DE) .......................... 10 2013 226 277

(51) Int. Cl.
*G01N 21/59* (2006.01)
*G01N 21/47* (2006.01)
(Continued)

(52) U.S. Cl.
CPC ............ *G01N 21/59* (2013.01); *G01N 21/47* (2013.01); *G01N 21/4795* (2013.01);
(Continued)

(58) Field of Classification Search
CPC .... G01N 21/59; G01N 21/47; G01N 21/6458; G01N 21/4795; G01N 2201/10;
(Continued)

(56) References Cited

U.S. PATENT DOCUMENTS 2,844,992 A * 7/1958 Bernhardt .............. G02B 21/02
359/387
4,515,445 A * 5/1985 Muller ................. G02B 21/088
359/386
(Continued)

FOREIGN PATENT DOCUMENTS

DE      19834279      3/2000
DE      102010063412  6/2012

OTHER PUBLICATIONS

Espacenet English Translation of EP0087574.*

*Primary Examiner* — Mohamed K Amara
(74) *Attorney, Agent, or Firm* — Hodgson Russ LLP (57) ABSTRACT

The invention relates to a method for tomographic investigation of a sample, in which method a sample is illuminated with an illuminating light bundle and in which a transmitted light bundle that contains the light of the illuminating light bundle transmitted through the sample is detected with a transmission detector. The invention further relates to an apparatus for tomographic investigation of a sample. Provision is made that the illuminating light bundle and the transmitted light bundle pass in opposite propagation directions through the same objective.

22 Claims, 5 Drawing Sheets

(51) Int. Cl.
*G01N 21/64* (2006.01)
*G02B 21/08* (2006.01)
*G02B 21/00* (2006.01)

(52) U.S. Cl.
CPC ..... *G01N 21/6458* (2013.01); *G02B 21/0028* (2013.01); *G02B 21/088* (2013.01); *G01N 2021/6491* (2013.01); *G01N 2201/0636* (2013.01); *G01N 2201/06113* (2013.01); *G01N 2201/10* (2013.01)

(58) Field of Classification Search
CPC . G01N 2201/0636; G01N 2201/06113; G01N 2021/6491; G02B 21/0028; G02B 21/088
See application file for complete search history.

(56) References Cited

U.S. PATENT DOCUMENTS

| | | | | |
|---|---|---|---|---|
| 5,731,588 | A * | 3/1998 | Hell | G01N 21/63 250/458.1 |
| 6,064,518 | A | 5/2000 | Stelzer et al. | |
| 9,057,879 | B2 * | 6/2015 | Knebel | G02B 21/002 |
| 9,201,011 | B2 * | 12/2015 | Kalkbrenner | G01N 21/6428 |
| 9,239,456 | B2 * | 1/2016 | Foelling | G02B 21/088 |
| 9,476,766 | B2 * | 10/2016 | Widzgowski | G01J 1/44 |
| 9,645,378 | B2 * | 5/2017 | Hilbert | G02B 21/06 |
| 9,664,620 | B2 * | 5/2017 | Lippert | G02B 21/06 |
| 9,766,180 | B2 * | 9/2017 | Wuite | G01N 21/6428 |
| 9,772,481 | B2 * | 9/2017 | Knebel | G02B 21/0032 |
| 9,880,378 | B2 * | 1/2018 | Taniguchi | G02B 21/24 |
| 9,921,161 | B1 * | 3/2018 | Feldkhun | G01N 21/6458 |
| 9,933,363 | B2 * | 4/2018 | Danuser | G01N 21/6428 |
| 2006/0033987 | A1 * | 2/2006 | Stelzer | G02B 21/06 359/385 |
| 2008/0049313 | A1 * | 2/2008 | Brehm | G01N 21/648 359/387 |
| 2008/0277567 | A1 | 11/2008 | Doran et al. | |
| 2009/0237765 | A1 * | 9/2009 | Lippert | G02B 21/06 359/213.1 |
| 2010/0201784 | A1 * | 8/2010 | Lippert | G02B 21/002 348/46 |
| 2010/0265575 | A1 * | 10/2010 | Lippert | G02B 21/16 359/385 |
| 2011/0031414 | A1 * | 2/2011 | Lippert | G02B 21/002 250/459.1 |
| 2011/0036996 | A1 * | 2/2011 | Wolleschensky | G01N 21/6458 250/459.1 |
| 2012/0049087 | A1 * | 3/2012 | Choi | G01N 21/4795 250/459.1 |
| 2013/0107358 | A1 | 5/2013 | Knebel et al. | |
| 2016/0153892 | A1 * | 6/2016 | Knebel | G02B 21/0032 359/385 |
| 2016/0214107 | A1 * | 7/2016 | Viasnoff | G01N 21/03 |
| 2016/0327779 | A1 * | 11/2016 | Hillman | G02B 21/367 |
| 2017/0160531 | A1 * | 6/2017 | Knebel | G01N 21/6458 |

* cited by examiner

METHOD AND APPARATUS FOR INVESTIGATING A SAMPLE BY MEANS OF OPTICAL PROJECTION TOMOGRAPHY

CROSS-REFERENCE TO RELATED APPLICATIONS

The present application is the U.S. national phase of International Application No. PCT/EP2014/078335 filed Dec. 17, 2014, which claims priority of German Application No. 10 2013 226 277.9 filed Dec. 17, 2013, the entirety of which is incorporated herein by reference.

FIELD OF THE INVENTION

The invention relates to a method for tomographic investigation of a sample, in which method a sample is illuminated with an illuminating light bundle and in which a transmitted light bundle that contains the light of the illuminating light bundle transmitted through the sample is detected with a transmission detector.

The invention furthermore relates to an apparatus for tomographic investigation of a sample, having a light source that generates an illuminating light bundle that illuminates the sample to be investigated, and having a transmission detector for detected a transmitted light bundle that contains light of the illuminating light bundle transmitted through the sample.

BACKGROUND OF THE INVENTION

WO 2012/027542 A2 discloses a microscope that simultaneously permits both optical tomographic investigation and SPIM investigation of a sample. This document concretely recites optical projection tomography (OPT). Disadvantageously, the microscope is of very complex construction; in particular, three objectives precisely aligned with one another are required simultaneously in order to focus illuminating light onto the sample and to receive detected light, emerging from the sample, for the respective detectors. The microscope moreover is not flexibly usable. For example, the sample must obligatorily be moved relative to the microscope so that three-dimensional images of the sample can be generated; this is cumbersome and not possible with every type of sample, since the experimentation space is restricted by the three objectives. Implementation of such a microscope in a conventional microscope configuration, in particular using a conventional microscope stand, is moreover not possible or at best possible only with difficulty, making the manufacture of such a microscope complex and costly.

SUMMARY OF THE INVENTION

The object of the present invention is to describe a method for investigating a sample by means of optical projection tomography which can be carried with a compact configuration, which is flexibly usable, and which nevertheless does not restrict the options for simultaneous utilization of other investigative methods, for example the SPIM technique, confocal observation technique, or multi-photon technique.

The object is achieved by way of a method of the kind recited previously which is characterized in that the illuminating light bundle and the transmitted light bundle are directed in opposite propagation directions through the same objective.

The object of the present invention is to describe an apparatus for investigating a sample by means of optical projection tomography which has a compact configuration, which is flexibly usable, and which nevertheless provides the option for simultaneous utilization of other investigative methods, for example the SPIM technique, confocal observation technique, or multi-photon technique.

This object is achieved by an apparatus that is characterized in that the illuminating light bundle and the transmitted light bundle proceed in opposite propagation directions through the same objective.

The invention has the advantage that it requires only a single objective for investigating a sample by means of optical projection tomography, so that a less restricted and easily accessible experimentation space is available for the sample.

The invention moreover has the advantage that the sample can easily be illuminated from opposite directions without great outlay, with no need to move the sample. This advantage results from the fact that illumination and detection do not take place on different sides of the sample plane, so that the light path can be reversed, for example, by a simple switchover by means of a beam deflecting device adjustable in terms of deflection angle, as will be explained in further detail below.

The invention furthermore has the advantage that it is implementable in a conventional microscope configuration, in particular including with the use of a conventional upright or inverted microscope stand; this has a positive effect on the complexity and cost for manufacturing the apparatus according to the present invention.

Preferably the illuminating light bundle is focused with the objective into the sample, and the transmitted light bundle is collimated by the objective.

A beam splitter, in particular a beam splitter plate, can be used in order to physically separate the transmitted light bundle coming from the objective from the illuminating light bundle to be propagated onto the objective, and to direct it onto a beam path leading to the transmission detector.

In a particular embodiment the illuminating light bundle, after it has passed through the objective, is deflected with an illuminating light deflecting means in such a way that after deflection it propagates at an angle different from zero degrees with respect to the optical axis of the objective. In particular, provision can advantageously be made that the illuminating light bundle, after it has passed through the objective, is deflected with an illuminating light deflecting means to the sample that is to be investigated. It is particularly advantageous if the illuminating light bundle, after it has passed through the objective, is deflected to the sample with the illuminating light deflecting means through an angle of 90 degrees (right angle) with respect to the optical axis of the objective. An embodiment of this kind is notable specifically for the fact that the light emerging from the sample perpendicularly to the propagation direction of the illuminating light proceeding through the sample proceeds, for example for SPIM image acquisition, parallel to the optical axis of the objective so that it can be collimated, in a straight-ahead direction with respect to the illuminating light bundle striking the objective, with a further objective and then detected. This type of arrangement of objectives is very similar to the conventional microscope configuration and can therefore be implemented easily and in a robust embodiment, in particular including by reconfiguration of an existing microscope, in particular of a scanning microscope.

Especially in an embodiment in which the illuminating light bundle coming from the objective is deflected to the sample with an illuminating light deflecting means, the transmitted light bundle coming from the sample can be directed to the objective with a transmitted light deflecting means. Provision can therefore be made in particular that the transmitted light bundle coming from the sample is deflected with a transmitted light deflecting means in such a way that after deflection it propagates parallel to the optical axis of the objective.

In order to obtain a sufficient number of measured values for calculating a three-dimensional projection tomogram of the sample, the sample is illuminated successively in time at different sample locations and/or with a different propagation direction of the illuminating light bundle. Preferably a light power value of the transmitted light bundle is measured with the transmission detector for each sample location and for each propagation direction of the illuminating light bundle.

In a very particularly advantageous embodiment the sample remains stationary in this context, while the position and/or the propagation direction of the illuminating light bundle relative to the sample are respectively modified. Although the sample is not moved, it is possible to obtain a sufficient quantity of transmittance information about the sample to allow a three-dimensional projection tomogram to be reconstructed from the information, the reason for this being that thanks to the present invention the sample can be illuminated substantially from at least three principal directions, namely in particular along the optical axis of the objective and from opposite directions transversely to the optical axis of the objective; this is explained in further detail later on.

Alternatively, however, it is also possible for the sample to be moved relative to the apparatus and relative to the illuminating light bundle in order to illuminate the sample successively in time at different sample locations and/or with a different propagation direction of the illuminating light bundle.

In a particular embodiment the position and/or the propagation direction of the illuminating light bundle is adjusted with a beam deflecting device that is placed in front of the objective and is adjustable in terms of deflection angle. A beam deflecting device of this kind can contain, for example, a gimbal-mounted mirror whose angular position is adjustable, for example, with galvanometers. It is also possible, for example, for the beam deflecting device to comprise two galvanometer mirrors having mutually perpendicular rotation axes. It is also possible for the beam deflecting device to be embodied as an acousto-optic beam deflecting device. According to a particular, independent inventive idea, the scanner of a scanning microscope is used as an adjustable beam deflecting device for modifying the position and/or the propagation direction of the illuminating light bundle.

In an advantageous embodiment the illuminating light bundle is firstly positioned and oriented with the adjustable beam deflecting device in such a way that after passing through the objective it strikes an illuminating light deflecting means and is deflected by it to the sample, and the transmitted light bundle emerging from the sample is directed with a transmitted light deflecting means to the objective. The illuminating light bundle is then positioned and oriented with the adjustable beam deflecting device in such a way that the light path proceeds in reverse, namely in such a way that the illuminating light bundle, after passing through the objective, strikes the transmitted light deflecting means and is directed by it to the sample, while the transmitted light bundle is directed with the illuminating light deflecting means to the objective. In brief: with this procedure the deflecting means exchange functions in order to reverse the light path. The sample can in this manner be illuminated from opposite directions with no need for it to be moved.

In order to allow the sample to be illuminated from as many directions as possible, a plurality of different or differently oriented deflecting means, which can function as illuminating light deflecting means and/or as transmitted light deflecting means, can be present. In particular, multiple deflecting means can be distributed around the sample. Alternatively or additionally, provision can also be made that a deflecting apparatus, for example constituting a beveled mirror, comprises a plurality of deflecting means. It is also possible to use a conical deflecting means, for example a conical mirror, that is arranged coaxially around the optical axis of the objective so that the direction of incidence of the illuminating light bundle onto the sample can be rotated, with the aid of a beam deflecting device adjustable in terms of deflection angle, 360 degrees around the sample which is likewise arranged on the optical axis. For this purpose, for example, the illuminating light bundle can be guided with the beam deflecting device in such a way that the incidence point on the surface of the conical mirror describes a circle.

Each of the deflecting means can comprise, for example, a flat or curved mirror. It is also possible in particular for the illuminating light deflecting means and the transmitted light deflecting means to be constituents of the same deflecting apparatus, for example of a beveled mirror.

Alternatively or in addition to the use of a beam deflecting device adjustable in terms of deflection angle in order to modify the position and/or propagation direction of the illuminating light bundle, provision can also be made that the position and/or propagation direction of the illuminating light bundle are adjusted by moving, in particular by displacing and/or by tilting, the illuminating light deflecting means.

Preferably the illuminating light bundle is round in cross section. It is also possible, however, for the illuminating light bundle to have a different cross-sectional shape. For example, the illuminating light bundle can be shaped with a cylindrical optic into a light ribbon for illumination for a SPIM image. Alternatively to this, as explained in detail below, a quasi-light ribbon for a SPIM image can be generated by rapidly waving back and forth an illuminating light bundle that is round in cross section.

For the case in which a cylindrical lens is used to shape the illuminating light bundle, the transmission detector can advantageously be embodied as an area detector or as a linear detector so that the entire spread-out transmitted light bundle can be captured simultaneously.

In a very particularly advantageous embodiment of the invention at least one SPIM image of at least one cross-sectional plane of the sample is generated simultaneously or sequentially with respect to the tomographic investigation. This has the advantage that information regarding the sample can be obtained, in particularly also simultaneously, with completely different investigation methods. More precise statements regarding the internal configuration and nature of the sample are thereby possible. In particular, errors and artifacts that possibly occur with one of the investigation methods can be recognized and corrected by way of the information obtained by means of the respective other investigation method.

The option of being able to use another investigation method in addition to a projection tomography investigation results in particular from the fact that thanks to the present invention there is available in the region of the sample a less restricted and easily accessible experimentation space in which a further objective can readily be arranged, in particular also coaxially with or parallel to the objective.

An embodiment in which a further objective is arranged coaxially with or parallel to the objective in order to collimate the detected light for a selective plane illumination microscopy (SPIM) image has the particular advantage that it can be of particularly compact configuration and that it is similar to the conventional microscope configuration; this permits the use of conventional microscope stands or makes it easy to retrofit existing microscope systems.

In order to generate a SPIM image, a sample is illuminated with a thin light ribbon while observation of the illuminated sample layer occurs perpendicularly to the plane of the illuminating light ribbon by detection of the fluorescent and/or scattered light. A three-dimensional image of the sample can be generated from the images of different sample layers, in particular from a stack of images of mutually parallel sample layers. The detector for acquiring the SPIM images can be embodied, for example, as a camera and/or as a CCD camera and/or as an SCMOS detector and/or as an area detector.

As already mentioned, a light ribbon for SPIM illumination can be shaped from the illuminating light bundle, for example, with a cylindrical optic.

Instead, however, a quasi-light ribbon can also be generated for SPIM illumination by waving the illuminating light bundle back and forth in a light ribbon plane. Provision can be made, for example, that firstly an illuminating light bundle that is largely round in cross section is generated, which bundle is waved back and forth by a beam deflecting device, which in particular can be the scanner of a scanning microscope, at a speed such that it forms a quasi-light ribbon. Provision can be made in particular that the illuminating light bundle is waved back and forth at a speed such that the detector receiving the detected light generates largely the same detected signals as in the context of illumination with a light ribbon generated, for example, with a cylindrical optic, and/or such that for the SPIM detector being used, the quasi-light ribbon is indistinguishable from a light ribbon generated, for example, with a cylindrical optic.

As already mentioned, advantageously a projection tomography investigation and a SPIM investigation of a sample can be performed simultaneously. Provision can be made in this context in particular that a quasi-light ribbon for illumination for a SPIM image is generated by waving the illuminating light bundle back and forth in a light ribbon plane, the transmitted light bundle simultaneously being respectively detected, for different illumination locations and/or for different propagation directions of the illuminating light bundle, for the tomographic investigation.

The use of a quasi-light ribbon produced from a largely round illuminating light bundle has the particular advantage that an additional optical system can be omitted, and also that quasi-light ribbons of largely arbitrary shape, in particular including curved ones, can be generated. The use of a quasi-light ribbon produced from a largely round illuminating light bundle is also advantageous for a simultaneous projection tomography investigation, since the respectively measured transmittance values can easily be associated with the relevant illumination locations and propagation directions of the illuminating light bundle.

In particular for a SPIM investigation but also in order to carry out other investigations of the sample simultaneously or sequentially with respect to a projection tomography investigation, provision can be made very generally that light emerging from the sample at an angle different from zero degrees with respect to the propagation direction of the illuminating light beam incident onto the sample, in particular at an angle of 90 degrees with respect to the propagation direction of the illuminating light beam incident onto the sample, passes through a further objective and is detected with a detector different from the transmission detector. The light can be, for example, fluorescent light and/or scattered light.

As already mentioned, the further objective can in particular advantageously be oriented so that the optical axis of the further objective is oriented at an angle of 90 degrees (right angle) with respect to the propagation direction of the illuminating light beam incident onto the sample, and/or so that the optical axis of the further objective is oriented parallel to or coaxially with the optical axis of the objective. It is in principle also possible, however, for the optical axis of the further objective to be oriented at another angle being different from zero degrees with respect to the propagation direction of the illuminating light beam incident onto the sample.

As already mentioned, thanks to the present invention the sample can be illuminated substantially from at least three principal directions, namely in particular along the optical axis of the objective and from opposite directions transversely to the optical axis of the objective. The procedure for illumination from opposite directions transversely to the optical axis of the objective has already been explained above. Illumination along the optical axis of the objective is accomplished without using the illumination deflecting means and the transmission deflecting means in a transmitted-light arrangement. The illuminating light bundle is oriented here in such a way that after passing through the objective it strikes the sample without deflection, and the transmitted light bundle travels in a straight-ahead direction to a further objective that can also be embodied as a condenser optic. After passing through the further objective the transmitted light bundle is directed into a beam path in which it travels to a detector, in particular to a further transmission detector.

The SPIM investigation described above is not possible during a projection tomography investigation in a transmitted light arrangement. The further objective to be used for the SPIM investigation can instead be used to collimate the transmitted light bundle and for that purpose can remain in its position, except for adaptations of focus that are possibly necessary. In a particular embodiment the SPIM detector is used in this context as a transmission detector.

The illuminating light deflecting means and/or the transmitted light deflecting means can advantageously be arranged on the objective or on the further objective. This has the advantage that large additional stand parts, which project from outside into the sample region and would themselves take up space, are not required. In addition, a placement on the objective or on the further objective ensures good stability, since the objectives themselves must already be held in stable fashion.

In a particular embodiment the illuminating light deflecting means and/or the transmitted light deflecting means are arranged movably, in particular displaceably and/or tiltably, on the objective or on the further objective. This kind of embodiment has the very particular advantage that the illumination location and/or the alignment of the illuminating light bundle can be modified by movement of the illuminating light deflecting means into a different position or into a different orientation. Analogously, the position and/or orientation of the transmitted light bundle can be modified by a movement of the transmitted light deflecting means into a different position or into a different orientation.

As already mentioned, the method according to the present invention can advantageously be executed with a scanning microscope or with a confocal scanning microscope. A non-descanned detector (NDD) that is possibly present in any case can be used in particular as a transmitted light detector and/or, especially if the NDD is embodied as an area detector, as a SPIM detector. The apparatus according to the present invention can in particular be constituted in part by a scanning microscope or by a confocal scanning microscope.

BRIEF DESCRIPTION OF THE DRAWING VIEWS

The subject matter of the invention is depicted schematically in the drawings and will be described below with reference to the Figures; identical or identically functioning elements are in most cases labeled with the same reference characters. In the drawings.

DETAILED DESCRIPTION OF THE INVENTION

Figure 1:
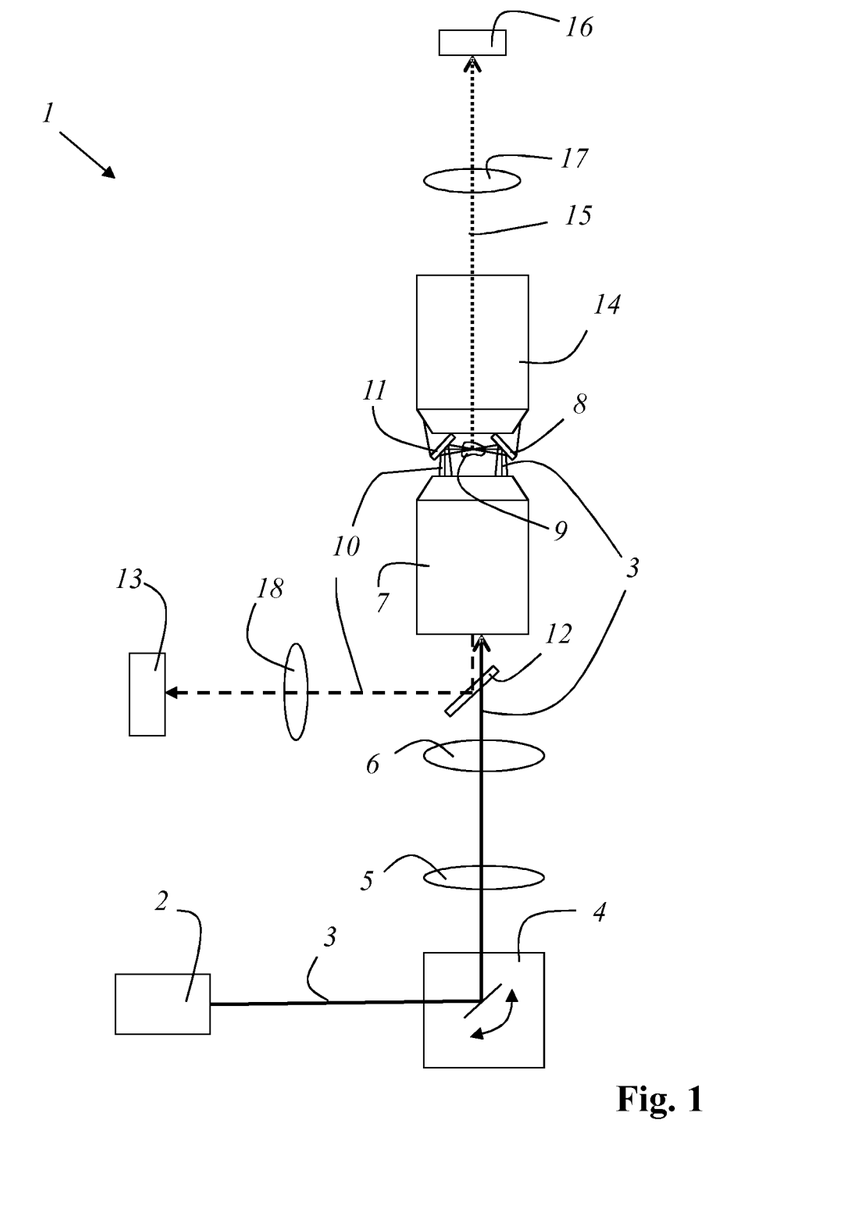
FIG. 1 is a schematic depiction to illustrate an exemplifying embodiment of the method according to the present invention upon illumination from a first principal direction.

FIG. 1 shows an exemplifying embodiment of an apparatus 1 according to the present invention. The apparatus comprises a light source 2 that can be embodied in particular as a laser. Light source 2 emits an illuminating light bundle 3 that is deflected by a beam deflecting device 4 adjustable in terms of deflection angle. After deflection, illuminating light bundle 3 proceeds through a scanning lens 5 and a tube lens 6, passes through a beam splitter 12, and travels to an objective 7 that focuses illuminating light bundle 3.

Beam deflecting device 4 is adjusted in such a way that illuminating light bundle 3 passes through the objective pupil of objective 7 at a tilt with respect to the optical axis so that it leaves objective 7 eccentrically, i.e. with a lateral offset with respect to the optical axis of objective 7, and then strikes an illuminating light deflecting means 8 that deflects illuminating light bundle 3, preferably through approximately 90 degrees, to a sample. Illuminating light bundle 3 has a focus in sample 9.

That portion of illuminating light bundle 3 which is transmitted through sample 9 leaves sample 9 as transmitted light bundle 10 and is deflected by a transmitted light deflecting means 11 to objective 7. Transmitted light bundle 10 proceeds through objective 7 in the same manner as illuminating light bundle 3, but in an opposite propagation direction.

After passing through objective 7, transmitted light bundle 10 is deflected at least in part by a beam splitter 12 to a lens 18 that focuses transmitted light bundle 10 onto a transmission detector 13.

In order to obtain measured values for calculating a three-dimensional projection tomogram of sample 9, sample 9 is illuminated successively in time at different sample locations and/or with a different propagation direction of illuminating light bundle 3, and for each sample location and for each propagation direction of illuminating light bundle 3 a light power level of transmitted light bundle 10 is respectively measured with transmission detector 13. For this, the spatial position and the propagation direction of illuminating light bundle 3 are continuously modified with the aid of beam deflecting device 4. Illuminating light deflecting means 8 and/or transmitted light deflecting means 11, both of which are arranged movably on a further objective 14, can additionally be adjusted for this purpose.

Simultaneously or sequentially with respect to a detection of transmitted light bundle 10, detected light 15 that emerges from sample 9 perpendicularly to the propagation direction of illuminating light beam 3 incident onto sample 9 is additionally detected with a detector 16 different from transmission detector 13. Detected light 15 passes through further objective 14 and is then focused by a further tube lens 17 onto detector 16. Concretely, a quasi-light ribbon for planar illumination of a sample layer of sample 9 for a SPIM image is generated by waving illuminating light bundle 3 back and forth with beam deflecting device 4 in a light ribbon plane perpendicular to the optical axis of objective 7. Detector 16 is embodied as a camera for acquiring an image of the illuminated sample layer.

Figure 2:
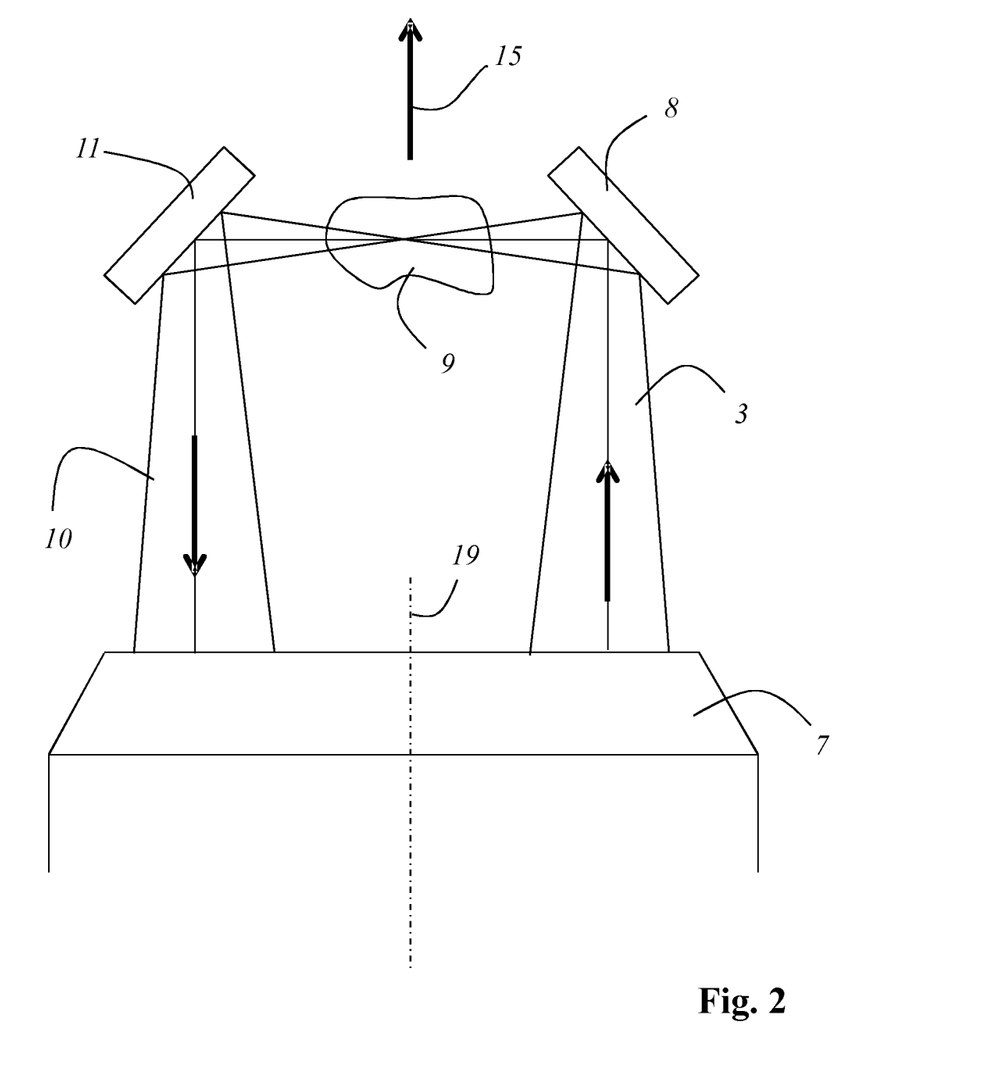
FIG. 2 is a schematic depiction to illustrate an exemplifying embodiment of the method according to the present invention upon illumination from a second principal direction opposite to the first.

FIG. 2 is a detailed depiction showing that illuminating light bundle 3 coming from objective 7 is deflected with an illuminating light deflecting means 8 to sample 9 at a right angle, and that transmitted light bundle 10 coming from sample 9 is deflected by a transmitted light deflecting means 11 to objective 7. Detected light 15 for a SPIM image proceeds in the direction of optical axis 19 of objective 7.

Figure 3:
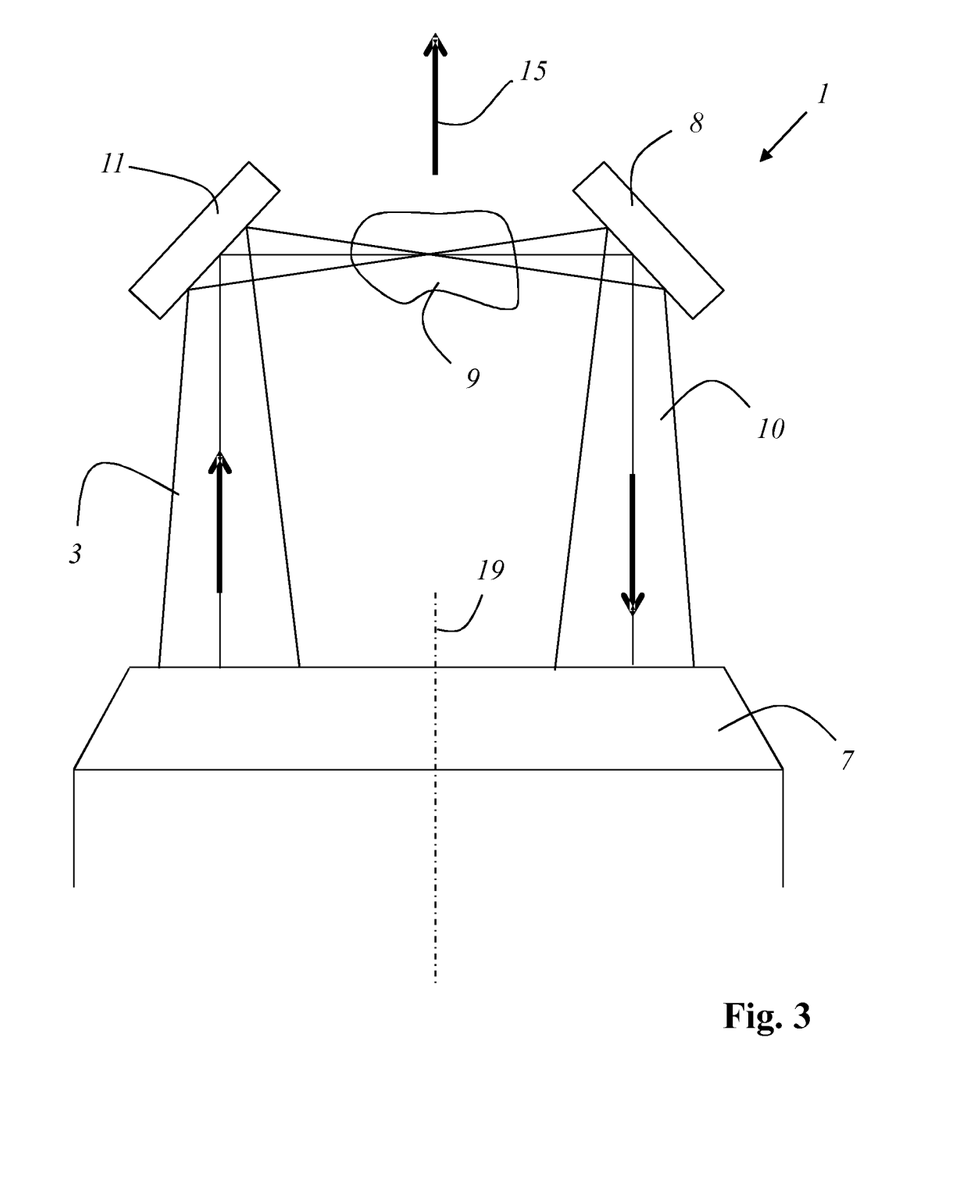
FIG. 3 schematically depicts an exemplifying embodiment of an apparatus according to the present invention.

FIG. 3 shows the manner in which sample 9 can be illuminated from the opposite direction with an illuminating light bundle 3. Illuminating light bundle 3 is positioned and oriented with the adjustable beam deflecting device 4 in such a way that the light path proceeds in reverse, namely in such a way that illuminating light bundle 3, after passing through objective 7, strikes transmitted light deflecting means 11 and is directed by it to sample 9, while transmitted light bundle 10 is directed by illuminating light deflecting means 8 to objective 7.

Figure 4:
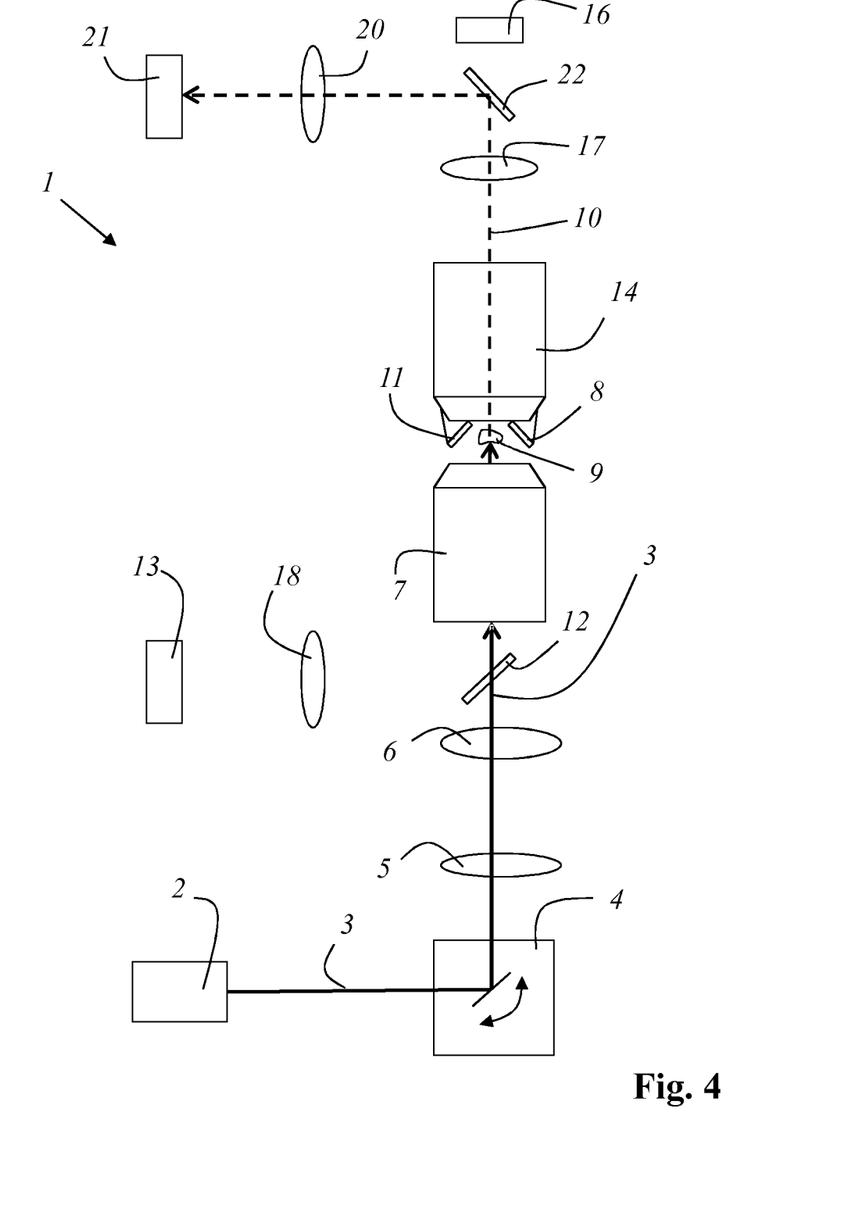
FIG. 4 is a schematic depiction to illustrate a further exemplifying embodiment of the method according to the present invention upon illumination from the first principal direction.

FIG. 4 shows the manner in which sample 9 can be illuminated from an additional principal illumination direction, namely substantially coaxially with the optical axis of objective 7. Such illumination is accomplished without the use of illumination deflecting means 8 and without the use of transmission deflecting means 11 in a transmitted light arrangement. For this purpose, illuminating light bundle 3 is oriented with beam deflecting device 4 in such a way that it proceeds centrally through the objective pupil of objective 7 and after passing through objective 7 strikes sample 9 without deflection, so that transmitted light bundle 10 travels to further objective 14 in a straight-ahead direction. By successive tilting of illuminating light bundle 3 in the objective pupil relative to the optical axis of objective 7, a lateral offset of illuminating light bundle 3 emerging from objective 7 can respectively be produced in order to successively transilluminate different sample regions. After passing through further objective 14, transmitted light bundle 10 is deflected with a mirror 22 and is then focused by an optic 20 onto a further transmission detector 21. The incidence location of illuminating light bundle 3 onto sample 9 and/or the propagation direction of illuminating light bundle 3 inside sample 9 can be varied with the aid of beam deflecting device 4 so that a transmittance value can be measured for each incidence location and/or each propagation direction, for subsequent tomographic reconstruction of an image of sample 9. It is therefore possible also to take into consideration for subsequent reconstruction, besides the measured values that were obtained in the context of illumination transversely to optical axis 19 of the objective, the measured values that were obtained in the context of the above-described transmitted light arrangement.

Figure 5:
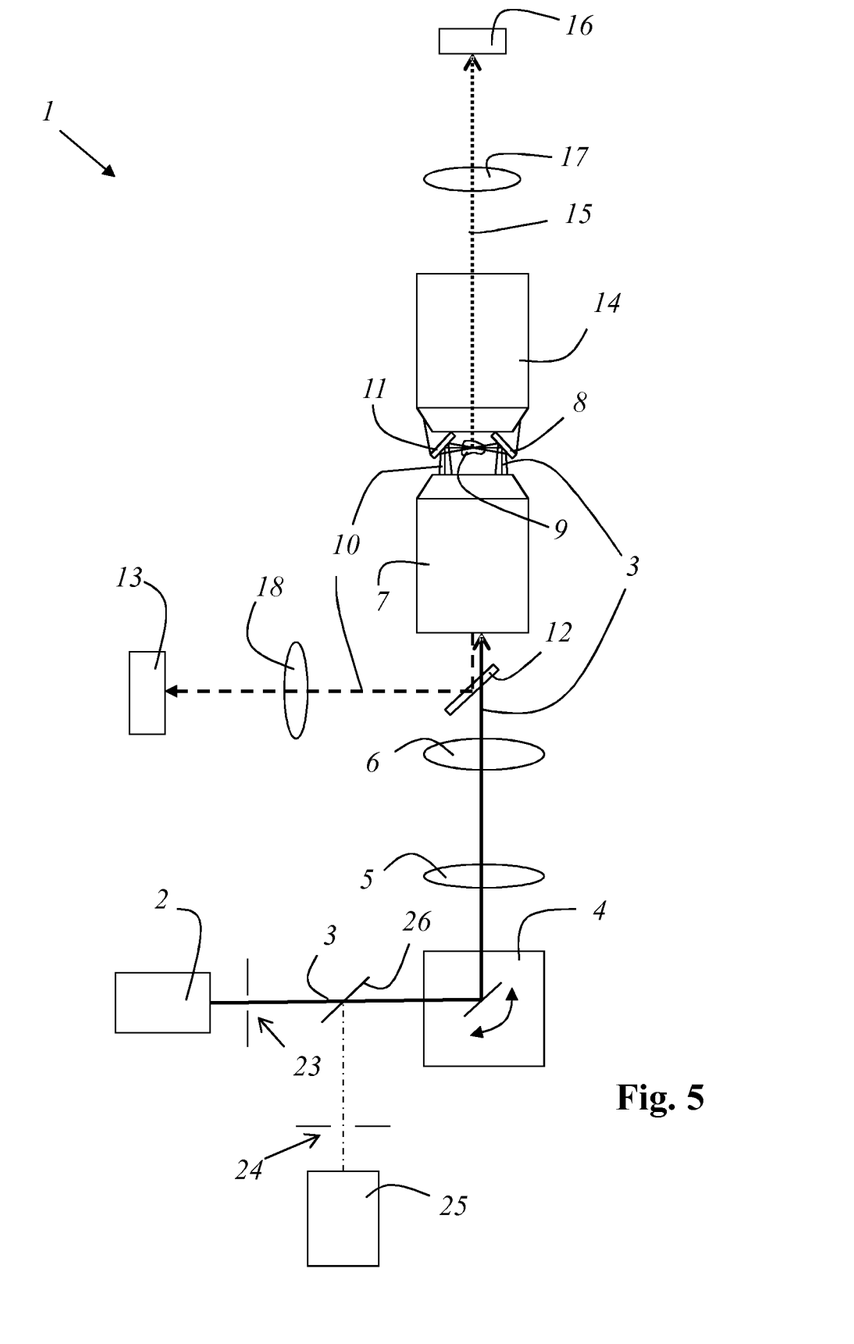
FIG. 5 shows an exemplifying embodiment of an apparatus according to the present invention on the basis of a confocal scanning microscope.

FIG. 5 shows an exemplifying embodiment of an apparatus 1 according to the present invention that bases on the basis of a confocal scanning microscope that, besides many components that are required for the investigations referred to above, also comprises an illumination pinhole 23, a detection pinhole 24, and a multi-band detector 25, as well as a dichroic beam splitter 26 for separating the excitation beam path from the detection beam path. These elements are not required, however, for the investigation methods described above. An ND detector of the confocal scanning microscope is used as transmitted light detector 13 for detecting transmitting light bundle 10. If an image-producing optic is used in the NDD beam path (tube lens), a spatially resolving detector (camera, CCD, CMOS, SCMOS) can also be used.

PARTS LIST

1 Apparatus according to the present invention
2 Light source
3 Illuminating light bundle
4 Adjustable beam deflecting device
5 Scanning lens
6 Tube lens
7 Objective
8 Illuminating light deflecting means
9 Sample
10 Transmitted light bundle
11 Transmitted light deflecting means
12 Beam splitter
13 Transmission detector
14 Further objective
15 Detected light
16 Detector
17 Further tube lens
18 Lens
19 Optical axis of objective 7
20 Optic
21 Further transmission detector
22 Mirror
23 Illumination pinhole
24 Detection pinhole
25 Multi-band detector
26 Dichroic beam splitter

What is claimed is:

1. A method for investigating a sample by means of optical projection tomography, in which method a sample is illuminated with an illuminating light bundle and in which a transmitted light bundle that contains the light of the illuminating light bundle transmitted through the sample is detected with a transmission detector,
   wherein the illuminating light bundle and the transmitted light bundle are directed in opposite propagation directions through a same objective; and
   wherein the illuminating light bundle, after passing through the objective, is deflected by an illuminating light deflecting means in such a way that after deflection the illuminating light bundle propagates such that a central axis of the illuminating light bundle defining a propagation direction of the illuminating light bundle is at an angle different from zero degrees with respect to an optical axis of the objective.

2. The method according to claim 1, wherein the illuminating light bundle, after passing through the objective, is deflected by the illuminating light deflecting means to the sample that is to be investigated.

3. The method according to claim 2, wherein the transmitted light bundle is deflected by a transmitted light deflecting means to the objective, and light emerging from the sample passes through a further objective, and wherein
   a. the illuminating light deflecting means and/or the transmitted light deflecting means is arranged, in particular movably, on the objective; or the illuminating light deflecting means and/or the transmitted light deflecting means is arranged, in particular movably, on the further objective; and/or
   b. the illuminating light deflecting means and the transmitted light deflecting means are constituents of a same deflecting apparatus.

4. The method according to claim 1, wherein
   a. the transmitted light bundle is deflected by a transmitted light deflecting means in such a way that after deflection the transmitted light bundle propagates parallel to the optical axis of the objective; and/or
   b. the transmitted light bundle is deflected by a transmitted light deflecting means to the objective.

5. The method according to claim 1, wherein
   a. the sample is illuminated successively in time at different sample locations and/or with a different propagation direction of the illuminating light bundle; or
   b. the sample is illuminated successively in time at different sample locations and/or with a different propagation direction of the illuminating light bundle, the sample remaining stationary and the position and/or the propagation direction of the illuminating light bundle relative to the sample being respectively modified.

6. The method according to claim 5, wherein
   a. the position and/or the propagation direction of the illuminating light bundle is adjusted by a beam deflecting device that is placed in front of the objective and is adjustable in terms of deflection angle; and/or
   b. the illuminating light bundle, after passing through the objective, is deflected by an illuminating light deflecting means to the sample that is to be investigated, and the position and/or the propagation direction of the illuminating light bundle is adjusted by moving the illuminating light deflecting means.

7. The method according to claim 1, wherein
   a. at least one selective plane illumination microscopy (SPIM) image of at least one cross-sectional plane of the sample is generated simultaneously or sequentially with respect to the tomographic investigation; and/or
   b. a quasi-light ribbon for illumination for a SPIM image is generated by waving the illuminating light bundle back and forth in a light ribbon plane; and/or c. a quasi-light ribbon for illumination for a SPIM image is generated by waving the illuminating light bundle back and forth in a light ribbon plane, the transmitted light bundle simultaneously being respectively detected, for different illumination locations and/or for different propagation directions of the illuminating light bundle, for the tomographic investigation.

8. The method according to claim 1, wherein
   a. light emerging from the sample at an angle different from zero degrees with respect to a propagation direction of the illuminating light bundle incident onto the sample passes through a further objective and is detected by a detector different from the transmission detector; or
   b. light emerging from the sample substantially at an angle of 90 degrees with respect to a propagation direction of the illuminating light bundle incident onto the sample passes through a further objective and is detected by a detector different from the transmission detector.

9. The method according to claim 8, wherein
   a. the optical axis of the further objective is oriented at an angle being different from zero degrees with respect to the propagation direction of the illuminating light bundle incident onto the sample; and/or
   b. the optical axis of the further objective is oriented at an angle of 90 degrees with respect to the propagation direction of the illuminating light bundle incident onto the sample; and/or
   c. the optical axis of the further objective is oriented parallel to or coaxially with the optical axis of the objective.

10. The method according to claim 1, wherein the sample is additionally illuminated with the illuminating light bundle, prior to or subsequently to the detection of the transmitted light bundle that proceeds through the same objective as the illuminating light bundle, in such a way that the transmitted light bundle propagates to a further objective and is detected after passing through the further objective.

11. The method according to claim 1, wherein the method is executed by a scanning microscope or by a confocal scanning microscope.

12. An apparatus for investigating a sample by means of optical projection tomography, the apparatus comprising:
    a light source that generates an illuminating light bundle that illuminates the sample to be investigated,
    a transmission detector for detecting a transmitted light bundle that contains light of the illuminating light bundle transmitted through the sample, and
    an objective having an optical axis,
    wherein the illuminating light bundle and the transmitted light bundle proceed in opposite propagation directions through the objective, and wherein an illuminating light deflecting means deflects the illuminating light bundle, after the illuminating light bundle has passed through the objective, in such a way that the illuminating light bundle propagates such that a central axis of the illuminating light bundle defining a propagation direction of the illuminating light bundle is at an angle different from zero degrees with respect to the optical axis of the objective.

13. The apparatus according to claim 12, wherein the illuminating light deflecting means deflects the illuminating light bundle, after it has passed through the objective, to the sample that is to be investigated.

14. The apparatus according to claim 13, wherein the transmitted light bundle is deflected by a transmitted light deflecting means to the objective, and light emerging from the sample passes through a further objective, and wherein
    a. the illuminating light deflecting means and/or the transmitted light deflecting means is arranged, in particular movably, on the objective; or the illuminating light deflecting means and/or the transmitted light deflecting means is arranged, in particular movably, on the further objective; and/or
    b. the illuminating light deflecting means and the transmitted light deflecting means are constituents of the same deflecting apparatus.

15. The apparatus according to claim 12, wherein
    a. a transmitted light deflecting means deflects the transmitted light bundle in such a way that it propagates parallel to the optical axis of the objective; and/or
    b. a transmitted light deflecting means deflects the transmitted light bundle to the objective.

16. The apparatus according to claim 12, wherein
    a. the sample is illuminatable successively in time at different sample locations and/or with a different propagation direction of the illuminating light bundle; or
    b. the sample is illuminatable successively in time at different sample locations and/or with a different propagation direction of the illuminating light bundle, the sample remaining stationary and the position and/or the propagation direction of the illuminating light bundle relative to the sample being respectively modified.

17. The apparatus according to claim 16, wherein
    a. the position and/or the propagation direction of the illuminating light bundle is adjustable with a beam deflecting device that is placed in front of the objective and is adjustable in terms of deflection angle; and/or
    b. the position and/or the propagation direction of the illuminating light bundle is adjustable by moving the illuminating light deflecting means.

18. The apparatus according to claim 12, wherein
    a. a detector different from the transmission detector receives, simultaneously or sequentially with respect to the tomographic investigation, light for at least one selective plane illumination microscopy (SPIM) image of at least one cross-sectional plane of the sample; and/or
    b. a beam deflecting device generates a quasi-light ribbon for illumination for a SPIM image by waving the illuminating light bundle back and forth in a light ribbon plane; and/or
    c. a beam deflecting device generates a quasi-light ribbon for illumination for a SPIM image by waving the illuminating light bundle back and forth in a light ribbon plane, the transmission detector simultaneously respectively detecting, for different illumination locations and/or for different propagation directions of the illuminating light bundle, the transmitted light bundle for the tomographic investigation.

19. The apparatus according to claim 12, wherein
    a. light emerging from the sample at an angle different from zero degrees with respect to a propagation direction of the illuminating light bundle incident onto the sample passes through a further objective and is detected by a detector different from the transmission detector; or
    b. light emerging from the sample substantially at an angle of 90 degrees with respect to a propagation direction of the illuminating light bundle incident onto the sample passes through a further objective and is detected by a detector different from the transmission detector.

20. The apparatus according to claim 19, wherein
a. an optical axis of the further objective is oriented at an angle being different from zero degrees with respect to the propagation direction of the illuminating light beam incident onto the sample; and/or
b. an optical axis of the further objective is oriented at an angle of 90 degrees (right angle) with respect to the propagation direction of the illuminating light beam incident onto the sample; and/or
c. an optical axis of the further objective is oriented parallel to or coaxially with the optical axis of the objective.

21. The apparatus according to claim 12, wherein a further transmission detector is arranged so as to receive and detect transmitted light that proceeds through a further objective rather than through the objective.

22. The apparatus according to claim 12, wherein the apparatus is constituted at least in part by a scanning microscope or by a confocal scanning microscope.

* * * * *